United States Patent [19]

Johnson et al.

[11] Patent Number: 5,177,206

[45] Date of Patent: Jan. 5, 1993

[54] PROCESS FOR THE PREPARATION OF SUBSTITUTED N-(ARYL)-1,2,4-TRIAZOLOPYRIMIDINE-2-SULFONAMIDES

[75] Inventors: Timothy C. Johnson, Concord; Wilmonte A. Nasutavicus, Lafayette, both of Calif.

[73] Assignee: DowElanco, Indianapolis, Ind.

[21] Appl. No.: 772,990

[22] Filed: Oct. 8, 1991

[51] Int. Cl.$^5$ .............................................. C07D 487/04
[52] U.S. Cl. .................................................. 544/263
[58] Field of Search ............................ 544/263; 71/92

[56] References Cited

U.S. PATENT DOCUMENTS

| | | | |
|---|---|---|---|
| 4,775,212 | 7/1988 | Kleschick et al. | 544/263 |
| 4,904,301 | 2/1990 | Pearson et al. | 544/263 |
| 4,910,306 | 3/1990 | McKendry | 544/263 |
| 4,937,350 | 6/1990 | Shankar | 548/263 |
| 5,008,352 | 4/1991 | Hendy | 525/534 |
| 5,010,195 | 4/1991 | VanHeertum et al. | 544/263 |

FOREIGN PATENT DOCUMENTS 0343752 11/1989 European Pat. Off. ............ 544/263
3801221 4/1986 U.S.S.R.

OTHER PUBLICATIONS

Cremlyn et al., Phosphorus and Sulfur, vol. 6, pp. 413-419 (1979).
Handy et al., Chem. Abstr., vol. 112 entry 100261(k) )1989).
Spince et al., Chem. Abstr., vol. 105 entry 17623(q) (1986).
Cremlyn et al., Chem. Abstr., vol. 91 entry 140463a (1979).

*Primary Examiner*—Donald G. Daus
*Attorney, Agent, or Firm*—Craig E. Mixan; Kenneth L. Loertscher

[57] ABSTRACT

The preparation of N-(aryl)-1,2,4-triazolopyrimidine-2-sulfonamides by the coupling of substituted 1,2,4-triazolopyrimidine-2-sulfonyl halides with aryl amines of substantially reduced nucleophilic reactivity is facilitated by conducting the reaction in the presence of a pyridine base and a catalytic amount of dimethyl sulfoxide.

9 Claims, No Drawings

PROCESS FOR THE PREPARATION OF SUBSTITUTED N-(ARYL)-1,2,4-TRIAZOLOPYRIMIDINE-2-SULFONAMIDES

FIELD OF THE INVENTION

The present invention concerns a process for the preparation of N-(aryl)-1,2,4-triazolopyrimidine-2-sulfonamides by the coupling of aryl amines with substituted 1,2,4-triazolopyrimidine-2-sulfonyl halides. More particularly, the present invention concerns the dimethyl sulfoxide catalyzed coupling of the amine and the sulfonyl halide in the presence of a pyridine base.

BACKGROUND OF THE INVENTION

Substituted N-(aryl)-1,2,4-triazolo[1,5-a]-pyrimidine-2-sulfonamides (I)

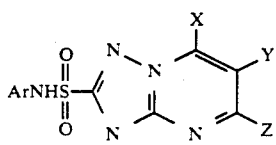

and substituted N-(aryl)-1,2,4-triazolo[1,5-c]-pyrimidine-2-sulfonamides (II),

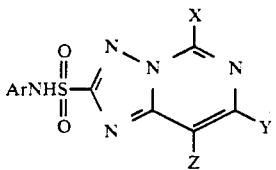

such as those described in U.S. Pat. Nos. 4,740,233 and 5,010,195, are valuable herbicides for the selective control of weeds in agronomic crops. Compounds of this family have generally been prepared by the conventional reaction between an aryl amine (III) and a substituted 1,2,4-triazolopyrimidine-2-sulfonyl chloride (IV)

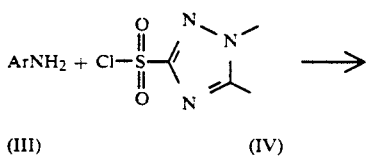

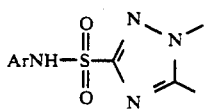

in the presence of a tertiary amine base (U.S. Pat. No. 4,740,233) or an excess of the aniline (British Patent 951,652). This procedure is generally satisfactory for the preparation of substituted 1,2,4-triazolopyrimidine-2-sulfonanilides when the substituted aniline employed is aniline itself or is a substituted derivative of aniline that has similar reactivity as a nucleophilic reagent. However, when the substituted aniline is of substantially reduced nucleophilic reactivity due to the presence of electron-withdrawing substituents on the ring, and especially, to the presence of such substituents in the positions ortho to the amino function, or when the aryl group is an electron-withdrawing heterocyclic group, this method is very slow and provides low yields of the desired products. This reactivity problem is particularly unfortunate because the most herbicidally potent substituted 1,2,4-triazolopyrimidine-2-sulfonamides possess just such substituents.

In order to circumvent this reactivity problem, a strong base, such as an alkali metal alkyl or an alkali metal hydride, capable of converting the poorly nucleophilic substituted aniline to its corresponding metal derivative, is employed in place of the tertiary amine base as described in U.S. Pat. No. 4,740,233. The metal derivative is preformed and then allowed to react with a substituted 1,2,4-triazolopyrimidine-2-sulfonyl halide. This procedure allows the compounds to be prepared, but it requires an excess of the metal derivative of the substituted aniline and is carried out below 0° C., and, therefore, is not commercially desirable.

Alternatively, the nucleophilicity of the aniline can be increased by converting it into the corresponding N-trialkylsilylaniline. U.S. Pat. No. 5,003,096 describes the enhanced reactivity of N-trialkylsilylanilines in their coupling with substituted 1,2,4-triazolo[1,5-a]pyrimidine-2-sulfonyl halides; U.S. Pat. No. 5,010,195 describes the similar enhanced reactivity in the case of the corresponding 1,2,4-triazolo[1,5-c]pyrimidines. Although this procedure allows a wider range of products containing electron-withdrawing groups to be prepared, it requires additional steps to synthesize the N-trialkylsilyl-anilines and to recover and recycle the valuable silicon-containing reagent.

In view of the valuable herbicidal properties of the sulfonamides (I) and (II), it is highly desirable to have a direct process which can be used to prepare a wide variety of materials in which the aryl groups contain electron-withdrawing substituents. Ideally, this process should avoid exceedingly long reaction times and the need of a strong base. Additionally, this process should avoid superfluous reaction steps and the recovery and recycle of expensive reagents.

SUMMARY OF THE INVENTION

The present invention concerns a process for the preparation of N-(aryl)-1,2,4-triazolopyrimidine-2-sulfonamides of the formula (V):

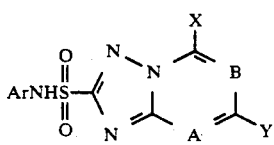

wherein
one of A or B is N and the other is C-Z,
X represents H, R, OR, SR or CF$_3$,
Y represents H, R, OR, F, Cl, Br or CF$_3$,
Z represents H, R, OR, F, Cl, Br, CF$_3$ or phenyl,
R represents a lower alkyl group optionally substituted with one or more halogen or with a lower alkoxy group, and
Ar is a substituted phenyl group of the formula:

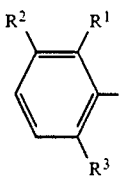

in which
R¹ represents H, F, Cl, Br, R, OR, SR or CO₂R,
R² represents H, R or OR,
R³ represents H, F, Cl, Br, CF₃, CO₂R or NO₂, and
R is as previously defined,
or Ar is a substituted pyrazole group (PRZ) of the formula:

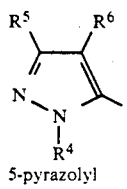

5-pyrazolyl

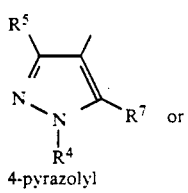

4-pyrazolyl

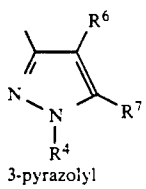

3-pyrazolyl in which
R⁴ represents R, phenyl or pyridinyl,
R⁵ represents H, NO₂ or CF₃,
R⁶ represents H, F, Cl, Br, I or CO₂R,
R⁷ represents H or R, and
R is as previously defined,
consisting of contacting a substituted 1,2,4-triazolopyrimidine-2-sulfonyl halide of the formula (VI):

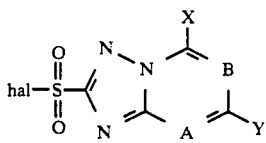

wherein
A, B, X, Y, Z and R are as previously defined, with an aryl amine of the formula

 ArNH₂ wherein
Ar is as previously defined, in an inert aprotic organic solvent in the presence of a pyridine base and of a catalytic amount of dimethyl sulfoxide (DMSO).

By conducting the reaction in the presence of a pyridine base and a catalytic amount of DMSO, it is possible to directly prepare a wide variety of N-(aryl)-1,2,4-triazolopyrimidine-2-sulfonamides containing electron-withdrawing substituents in the N-(aryl) group.

DETAILED DESCRIPTION OF THE INVENTION

As used herein, the terms "lower alkyl" and "lower alkoxy" are meant to designate straight or branched, saturated alkyl or alkoxy groups of from 1 to 4 carbon atoms.

Where individual members of the halogen family are not specifically listed, the general terms "halogen", "halide", "halo" and "hal", as used herein, are meant to be construed as being limited to chloro and bromo.

By pyridine base is meant pyridine or a methylpyridine such as the picolines or the lutidines. Pyridine itself is generally preferred.

The substituted 1,2,4-triazolopyrimidine-2-sulfonyl halides (VI)

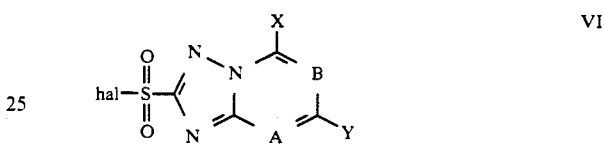

wherein
one of A or B is N and the other is C-Z,
X represents H, R, OR, SR or CF₃,
Y represents H, R, OR, F, Cl, Br or CF₃,
Z represents H, R, OR, F, Cl, Br, CF₃ or phenyl, and
R represents a lower alkyl group optionally substituted with one or more halogen or with a lower alkoxy group,
utilized in the process of this invention are known compounds and can be prepared as described in U.S. Pat. Nos. 4,886,883, 4,954,163 or 5,010,195 or by other conventional methods. Examples of suitable reactants include the following: 8-chloro-7-methoxy-5-methyl-1,2,4-triazolo[1,5-c]pyrimidine-2-sulfonyl chloride; 8-chloro-5-methoxy-1,2,4-triazolo-[1,5-c]-pyrimidine-2-sulfonyl chloride; 7-fluoro-5-methoxy-1,2,4-triazolo[1,5-c]pyrimidine-2-sulfonyl chloride; 7-chloro-5,8-dimethoxy-1,2,4-triazolo[1,5-c]pyrimidine-2-sulfonyl chloride; 5-methoxy-1,2,4-triazolo[1,5-c]-pyrimidine-2-sulfonyl chloride; 7-chloro-5-methoxy-1,2,4-triazolo[1,5-c]pyrimidine-2-sulfonyl chloride; 7-chloro-5-ethoxy-1,2,4-triazolo[1,5-c]pyrimidine-2-sulfonyl chloride; 5-methoxy-7-methyl-1,2,4-triazolo-[1,5-c]pyrimidine-2-sulfonyl chloride; 5-ethoxy-7-methyl-1,2,4-triazolo[1,5-c]pyrimidine-2-sulfonyl chloride; 5-chloro-7-methoxy-1,2,4-triazolo[1,5-c]pyrimidine-2-sulfonyl chloride; 8-bromo-5-chloro-7-methoxy-1,2,4-triazolo[1,5-c]pyrimidine-2-sulfonyl chloride; 5,7-dimethyl-1,2,4-triazolo[1,5-a]pyrimidine-2-sulfonyl chloride; 5-methyl-1,2,4-triazolo[1,5-a]pyrimidine-2-sulfonyl chloride; 5-methyl-7-trifluoromethyl-1,2,4-triazolo[1,5-a]pyridimine-2-sulfonyl bromide; 1,2,4-triazolo[1,5-a]pyrimidine-2-sulfonyl chloride; 5-methoxy-7-butyl-1,2,4-triazolo[1,5-a]pyrimidine-2-sulfonyl bromide; 6-chloro-1,2,4-triazolo[1,5-a]-pyrimidine-2-sulfonyl chloride; 5-methylethyl-7-methylthio-1,2,4-triazolo[1,5-a]pyrimidine-2-sulfonyl chloride; 5,7-dimethyl-6-fluoro-1,2,4-triazolo[1,5-a]-pyrimidine-2-sulfonyl chloride; and 5,7-dimethoxy-1,2,4-triazolo[1,5-a]pyrimidine-2-sulfonyl chloride. Preferred compounds are those in which X represents H, R or OR; Y represents H, R, OR, F or Cl; Z represents H, R, OR, F, Cl or Br; and R represents CH₃ or CH₂CH₃. When A is C-Z and B is N, X is preferably OR. When A is N and B is C-Z, Z is preferably H. The sulfonyl chlorides are preferred to the bromides.

Similarly, the aryl amines (III)

wherein
Ar is a substituted phenyl group of the formula:

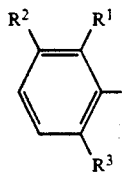

in which
R¹ represents H, F, Cl, Br, R, OR, SR or CO₂R,
R² represents H, R or OR,
R³ represents H, F, Cl, Br, CF₃, CO₂R or NO₂, and
R represents a lower alkyl group optionally substituted with one or more halogen or with a lower alkoxy group,
or Ar is a substituted pyrazole group (PRZ) of the formula

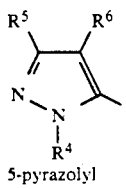
5-pyrazolyl

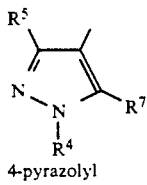
4-pyrazolyl

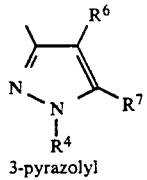
3-pyrazolyl in which
R⁴ represents R, phenyl or pyridinyl,
R⁵ represents H, NO₂ or CF₃,
R⁶ represents H, F, Cl, Br, I or CO₂R,
R⁷ represents H or R, and
R is as previously defined,
used in the process of this invention are also known compounds and can be prepared by conventional methods. Suitable anilines and pyrazoles include, for example, the following: 2,6-dichloroaniline; 2,6-difluoroaniline; 2,6-dibromoaniline; 2-fluoro-6-chloroaniline; 2,6-dichloro-3-methylaniline; 2,6-difluoro-3-methylaniline; methyl 3-chloroanthranilate; methyl 3-fluoroanthranilate; methyl 3-methylanthranilate; 2-methoxy-6-trifluoromethylaniline; 2,3-dimethyl-6-nitroaniline; 1-methyl-3-aminopyrazole; 1-methyl-4-bromo-3-aminopyrazole; 1-methyl-4-iodo-3-aminopyrazole; 1-methyl-3-nitro-4-aminopyrazole; 1,5-dimethyl-3-trifluoromethyl-4-aminopyrazole; 1-methyl-4-bromo-5-aminopyrazole; 1-(2-pyridinyl)-4-bromo-5-aminopyrazole; and 1-phenyl-4-bromo-5-aminopyrazole. When Ar is a substituted phenyl group, the preferred compounds are those in which R¹ represents F, Cl or R; R² represents H or R; R³ represents F, Cl, CF₃, CO₂R or NO₂; and R represents CH₃ or CH₂CH₃, most preferably CH₃. When Ar is a substituted pyrazole group, the preferred compounds are the 3- and 5-pyrazolyl compounds in which R⁴ represents R; R⁵ and R⁷ represent H; R⁶ represents H, F, Cl, Br or I; and R represents CH₃ or CH₂CH₃, most preferably CH₃.

The process is usually conducted by placing the substituted 1,2,4-triazolopyrimidine-2-sulfonyl halide, the aryl amine and an inert solvent in a vessel and then adding the pyridine base and the catalytic amount of dimethyl sulfoxide. The mixture is allowed to react, typically at ambient temperature. After a substantial amount of product sulfonamide has been formed or a substantial amount of sulfonyl halide has been consumed, the desired product (V) is recovered by standard procedures. For example, if a water-soluble solvent has been employed, it is generally first replaced by a water-immiscible solvent. The resulting solution can be washed with dilute acid and water and dried; the product can be recovered by evaporation of the solvent. The recovered product can be purified, if desired, by dissolution in dilute aqueous base, filtration and/or extraction with an immiscible organic solvent, such as diethyl ether, and reprecipitation with a dilute aqueous acid. Alternatively, the desired compounds can be purified by recrystallization and by other commonly used methods.

Approximately equimolar quantities of substituted 1,2,4-triazolopyrimidine-2-sulfonyl halide and of aryl amine are generally used in the process, although substantial excesses of one or the other may be employed. It is often convenient, for example, to use up to a 2 or 3 fold excess of aryl amine with respect to the sulfonyl chloride. This is particularly so when it is desirable to assure complete reaction of the more valuable reactant. The pyridine base is generally employed in an amount from 1 to 3 moles per mole of 1,2,4-triazolopyrimidine-2-sulfonyl halide. Dimethyl sulfoxide is typically used in an amount from 0.05 to 0.5 moles per mole of 1,2,4-triazolopyrimidine-2-sulfonyl halide; amounts over about 0.5 moles per mole of sulfonyl halide are usually deleterious.

Temperature is not critical; the reaction typically takes place at temperatures between 0° and 60° C. and is most conveniently carried out at ambient temperature.

The reaction is usually conducted in a moderately polar aprotic organio solvent which is inert both to the reactants and to the reaction conditions. Suitable inert aprotic organic solvents include: alkyl nitriles, such as, for example, acetonitrile; ethers, such as, for example, dioxane or tetrahydrofuran: or carboxylic acid esters, such as, for example, ethyl acetate.

The following examples are presented to illustrate the invention and should not be construed as limiting the scope of the invention. All melting points are uncorrected.

EXAMPLE 1

Preparation of N-(2,6-Dichlorophenyl)-8-bromo-5-methoxy-1,2,4-triazolo[1,5-c]-pyrimidine-2-sulfonamide 2,6-Dichloroaniline (1.76 grams (g), 10.9 mmol), 2-chlorosulfonyl-8-bromo-5-methoxy-1,2,4-triazolo[1,5-c]pyrimidine (1.5 g, 4.6 mmol), and 30 milliliters (mL) of dry acetonitrile were placed in a 100 mL flask equipped with a gas inlet adapter and a magnetic stirring bar. Pyridine (0.74 mL, 9.2 mmol) and dimethyl sulfoxide (0.08 mL, 1.2 mmol) were added with stirring under nitrogen and the mixture was allowed to react for 1.25 hours (hr). The volatiles were then removed by evaporation under reduced pressure and the residue was dissolved in 100 mL of methylene chloride. The solution obtained was extracted 3 times with 75 mL of 1N HCl and once with 100 mL of water, dried over MgSO4, filtered, and concentrated by evaporation under reduced pressure to obtain a yellow solid. This solid was diluted with 100 mL of hexane and, after standing for 1 hr, the hexane was removed by filtration and the solids washed with more hexane and dried to obtain 1.1 g (52 percent yield) of the title compound as a yellow solid melting at 192°–196° C.

EXAMPLE 2

Preparation of N-(Phenyl)-1,2,4-triazolo-[1,5-c]pyrimidine-2-sulfonamides

The compounds listed in Table 1 were prepared from the corresponding starting materials in accordance with the procedure described in Example 1.

TABLE 1

N-(PHENYL)-1,2,4-TRIAZOLO[1,5-c]PYRIMIDINE-2-SULFONAMIDES

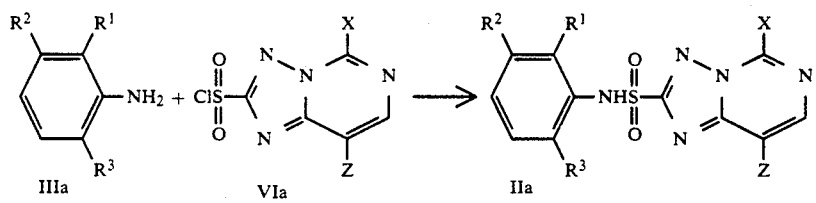

IIIa    VIa    IIa

| Triazolo-pyrimidine Substituents | | Phenyl Substituents | | | Yield % of theory | Appearance | Melting Point °C. | mole ratio IIIa:VIa:pyr: DMSO |
|---|---|---|---|---|---|---|---|---|
| X | Z | $R^1$ | $R^2$ | $R^3$ | | | | |
| $OCH_3$ | Cl | $NO_2$ | H | $CH_3$ | 40 | yellow powder | 205–209 (d) | 2:1:2:0.25 |
| $OCH_3$ | Cl | $CH_3$ | $CH_3$ | $NO_2$ | 35 | yellow solid | 197–199 (d) | 2:1:2:0.25 |
| $OCH_3$ | F | $CH_3$ | $CH_3$ | $NO_2$ | 34 | yellow solid | 224–226 (d) | 1.2:1:2:0.1 |
| $OCH_3$ | $CH_2F$ | F | H | F | 56 | tan powder | 202–204 (d) | 2:1:1:0.2 |
| $OCH_3$ | $OCH_3$ | Cl | H | Cl | 25 | yellow solid | 188–192 (d) | 2:1:1:0.13 |
| $OCH_3$ | $C_6H_5$ | Cl | H | Cl | 54 | yellowish solid | 200–202 | 2:1:1:0.1 |
| $OCH_3$ | $CH_2OCH_3$ | Cl | H | Cl | 22 | yellowish solid | 180–183 | 3:1:1:0.2 |
| $OCH_3$ | H | Cl | H | $CO_2CH_3$ | 43 | yellow solid | 190–201 (d) | 2:1:2:0.2 |
| $OCH_3$ | I | $CO_2CH_3$ | H | F | 44 | yellow powder | 154–156 (d) | 2:1:1:0.1 |
| $OCH_2CH_3$ | Cl | F | $CH_3$ | F | 50 | white powder | 225–226 (d) | 2:1:2:0.3 |
| $OCH_3$ | Br | Cl | H | Cl | 52 | yellow solid | 192–196 (d) | 2:1:2:0.3 |
| $OCH_3$ | Cl | $OCH_3$ | H | F | 57 | orange solid | 203–205 | 1.3:1:2:0.3 |
| $OCH_3$ | Cl | $SCH_3$ | H | F | 33 | white solid | 234–236 (d) | 1.1:1:2:0.2 |
| $OCH_3$ | Cl | F | H | H | 64 | orange solid | 160–162 (d) | 2:1:2:0.2 |
| $OCH_3$ | F | $CF_3$ | H | $OCH_3$ | 48 | yellow solid | 193–195 (d) | 2:1:2:0.1 |
| $OCH_3$ | $CH_3$ | F | H | $CO_2CH_3$ | 56 | tan solid | 175–178 (d) | 3:1:2:0.1 |
| $OCH_3$ | F | $CH_2OCH_3$ | H | Cl | 42 | yellow powder | 140–143 | 2:1:1:0.1 |

EXAMPLE 3

Preparation of N-(4-bromo-1-methylpyrazol-3-yl)-7-chloro-5-methoxy-1,2,4-triazolo-[1,5-c]pyrimidine-2-sulfonamide Pyridine (1.08 g, 8 mmol) and dimethyl sulfoxide (0.2 g) were added to a solution of 7-chloro-5-methoxy-1,2,4-triazolo[1,5-c]pyrimidine-2-sulfonyl chloride (1.0 g, 4.0 mmol) and 3-amino-4-bromo-1-methylpyrazole (0.7 g, 4.0 mmol) in 10 mL of acetonitrile with stirring at ambient temperature and the mixture was allowed to react overnight. The mixture was then concentrated by evaporation under reduced pressure and the residue was taken up in methylene chloride. The resulting solution was extracted with water and dried over MgSO$_4$. The volatile materials were then removed by evaporation under reduced pressure and the solid residue was extracted with diethyl ether and with water, recovered by filtration, and dried under reduced pressure to obtain 0.38 g (25 percent yield) of the title compound as a white solid melting at 230°–232° C.

EXAMPLE 4

Preparation of N-(Pyrazolyl)-1,2,4-triazolo-[1,5-c]pyrimidine-2-sulfonamides

The compounds listed in Table 2 were prepared from the corresponding starting materials in accordance with the procedure described in Example 3.

TABLE 2

N-PYRAZOLYL-1,2,4-TRIAZOLO[1,5-c]PYRIMIDINE-2-SULFONAMIDES

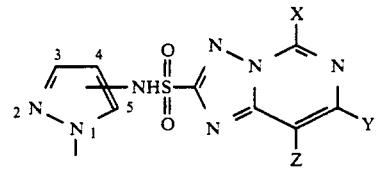

| X | Y | Z | 3-, 4-, or 5-PRZ | PRZ SUBSTITUENTS | YIELD, % OF THEORY | APPEARANCE | MELTING POINT, °C. |
|---|---|---|---|---|---|---|---|
| OCH$_3$ | Cl | H | 3- | 1-CH$_3$ | — | white solid | 185–187 |
| OCH$_3$ | Cl | H | 3- | 1-CH$_3$, 4-Br | 25 | pink solid | 230–232 |
| OCH$_3$ | Cl | H | 3- | 1-CH$_3$, 4-CO$_2$CH$_3$ | 16 | tan solid | 158–160 |
| OCH$_3$ | CH$_3$ | H | 3- | 1-CH$_3$, 4-Br | 40 | pink solid | 191–193 |
| OCH$_3$ | H | Cl | 5- | 1-CH$_3$, 4-Br | 48 | tan solid | 210–212 |
| OCH$_3$ | H | CH$_3$ | 5- | 1-CH$_3$, 4-Br | 98 | tan solid | 207–209 |
| OCH$_3$ | H | Cl | 4- | 1-CH$_3$, 3-NO$_2$ | 44 | tan solid | 120–122 |
| OCH$_3$ | H | Br | 5- | 1-CH$_3$, 4-Br | 56 | tan solid | 221–222 |
| OC$_2$H$_5$ | F | H | 5- | 1-CH$_3$, 4-Br | 30 | tan solid | 220–221 |
| OC$_2$H$_5$ | F | H | 4- | 1,5-diCH$_3$, 3-CF$_3$ | 66 | tan solid | 196–198 |
| OC$_2$H$_5$ | F | H | 3- | 1-CH$_3$, 4-Br | 33 | tan solid | 220–221 (d) |
| OCH$_3$ | H | Br | 3- | 1-CH$_3$, 4-Br | 60 | tan solid | 204–206 (d) |
| OCH$_3$ | Cl | H | 4- | 1,5-diCH$_3$, 3-CF$_3$ | 31 | tan solid | 224–225 |
| OCH$_3$ | H | F | 3- | 1-CH$_3$, 4-Br | 95 | white solid | 191–193 |
| OCH$_3$ | H | Cl | 3- | 1-CH$_3$, 4-Br | 41 | pink solid | 201–203 |
| OCH$_3$ | H | CH$_3$ | 3- | 1-CH$_3$, 4-Br | 39 | white solid | 210–212 |
| OCH$_3$ | C$_2$H$_5$ | H | 5- | 1-CH$_3$, 4-Br | 25 | white solid | 192–194 |
| OCH$_3$ | H | Cl | 3- | 1-CH$_3$, 4-I | 49 | white solid | 201–203 |
| OC$_2$H$_5$ | F | H | 3- | 1-CH$_3$, 4-I | 48 | white solid | 217–218 (d) |
| OC$_2$H$_5$ | H | CH$_3$ | 3- | 1-CH$_3$, 4-Br | 44 | white solid | 220–222 (d) |
| OCH$_3$ | Cl | H | 3- | 1-CH$_3$, 4-I | 51 | tan solid | 193–184 (d) |
| OCH$_3$ | H | OCH$_3$ | 3- | 1-CH$_3$, 4-Br | 31 | white solid | 209–211 (d) |
| OC$_2$H$_5$ | H | H | 3- | 1-CH$_3$, 4-Br | 29 | white solid | 230–232 |
| OC$_2$H$_5$ | H | H | 3- | 1-CH$_3$, 4-I | 37 | white solid | 232–234 |
| OCH$_3$ | I | H | 3- | 1-CH$_3$, 4-Br | 28 | tan solid | 259–261 |
| OCH$_3$ | I | H | 3- | 1-CH$_3$, 4-I | 20 | tan solid | 217–219 |
| OCH$_3$ | H | I | 3- | 1-CH$_3$, 4-Br | 42 | white solid | 233–235 |
| OC$_2$H$_5$ | H | OCH$_3$ | 3- | 1-CH$_3$, 4-Br | 54 | white solid | 223–225 |

TABLE 2-continued
N-PYRAZOLYL-1,2,4-TRIAZOLO[1,5-c]PYRIMIDINE-2-SULFONAMIDES

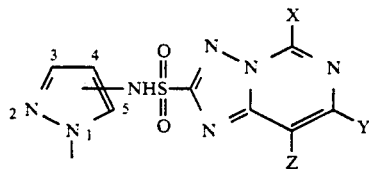

| X | Y | Z | 3-, 4-, or 5-PRZ | PRZ SUBSTITUENTS | YIELD, % OF THEORY | APPEARANCE | MELTING POINT, °C. |
|---|---|---|---|---|---|---|---|
| OC$_2$H$_5$ | CH$_3$ | H | 3- | 1-CH$_3$, 4-Br | 18 | white solid | 223–225 |
| OC$_2$H$_5$ | F | H | 5- | 1-(2-pyridinyl), 4-Br | 35 | white solid | 204–206 |
| OCH$_3$ | H | Cl | 5- | 1-C$_6$H$_5$, 4-Br | 26 | white solid | 240–242 |

EXAMPLE 5

Preparation of N-(2,6-Dichlorophenyl)-8-bromo-5-methoxy-1,2,4-triazolo[1,5-c]-pyrimidine-2-sulfonamide 2,6-Dichloroaniline (0.49 g, 3.1 mmol), 2-chlorosulfonyl-8-bromo-5-methoxy-1,2,4-triazolo[1,5-c]-pyrimidine (1.0 g, 3.1 mmol), and 20 mL of dry acetonitrile were placed in a 100 mL flask equipped with a gas inlet adapter and a magnetic stirring bar. Pyridine (0.50 mL, 6.2 mmol) and dimethyl sulfoxide (0.06 mL, 0.8 mmol) were added with stirring under nitrogen and the mixture was allowed to react for 1 hr. The volatiles were then removed by evaporation under reduced pressure and the residue was dissolved in 150 mL of methylene chloride. The solution obtained was extracted 2 times with 100 mL of 1N HCl and once with 100 mL of water, dried over MgSO$_4$, filtered, and concentrated by evaporation under reduced pressure to obtain a yellow solid. This solid was stirred with 200 mL of hexane and filtered to give 0.38 g (27 percent yield) of the title compound as a yellow solid melting at 198°–200° C. (d).

EXAMPLE 6

Preparation of N-(2,6-Dichlorophenyl)-8-bromo-5-methoxy-1,2,4-triazolo[1,5-c]-pyrimidine-2-sulfonamide 2,6-Dichloroaniline (1.0 g, 6.2 mmol), 2-chlorosulfonyl-8-bromo-5-methoxy-1,2,4-triazolo[1,5-c]-pyrimidine (1.0 g, 3.1 mmol), and 20 mL of dry acetonitrile were placed in a 100 mL flask equipped with a gas inlet adapter and a magnetic stirring bar. The solution was cooled to 0° C. Pyridine (0.50 mL, 6.2 mmol) and dimethyl sulfoxide (0.06 mL, 0.8 mmol) were added with stirring under nitrogen and the mixture was allowed to react for 1 hr at 0° C. The volatiles were then removed by evaporation under reduced pressure and the residue was dissolved in 150 mL of methylene chloride. The solution obtained was extracted 2 times with 100 mL of 1N HCl and once with 100 mL of water, dried over MgSO$_4$, filtered, and concentrated by evaporation under reduced pressure to obtain a yellow solid. This solid was stirred with 200 mL of hexane and filtered to give 0.37 g (26 percent yield) of the title compound as a yellow solid melting at 196°–198° C. (d).

EXAMPLE 7

Preparation of N-(2,6-Dichlorophenyl)-8-bromo-5-methoxy-1,2,4-triazolo[1,5-c]-pyrimidine-2-sulfonamide 2,6-Dichloroaniline (1.0 g, 6.2 mmol), 2-chlorosulfonyl-8-bromo-5-methoxy-1,2,4-triazolo[1,5-c]-pyrimidine (1.0 g, 3.1 mmol), and 20 mL of dry acetonitrile were placed in a 100 mL flask equipped with a gas inlet adapter and a magnetic stirring bar. Pyridine (0.50 mL, 6.2 mmol) and dimethyl sulfoxide (0.06 mL, 0.8 mmol) were added with stirring under nitrogen and the mixture was allowed to react for 3.5 hr. The volatiles were then removed by evaporation under reduced pressure and the residue was dissolved in 150 mL of methylene chloride. The solution obtained was extracted 2 times with 100 mL of 1N HCl and once with 100 mL of water, dried over MgSO$_4$, filtered, and concentrated by evaporation under reduced pressure to obtain a yellow solid. This solid was stirred with 200 mL of hexane and filtered to give 0.48 g (34 percent yield) of the title compound as a yellow solid melting at 196°–198° C. (d).

EXAMPLE 8

Preparation of N-(2,6-Dichlorophenyl)-5-methyl-1,2,4-triazolo[1,5-a]pyrimidine-2-sulfonamide 2,6-Dichloroaniline (2.78 g, 17.2 mmol), 2-chlorosulfonyl-5-methyl-1,2,4-triazolo[1,5-a]pyrimidine (2.0 g, 8.6 mmol), and 30 mL of dry acetonitrile were placed in a 100 mL flask equipped with a gas inlet adapter and a magnetic stirring bar. Pyridine (1.39 mL, 17.2 mmol) and dimethyl sulfoxide (0.15 mL, 2.2 mmol) were added with stirring under nitrogen and the mixture was allowed to react for 1.0 hr. The volatiles were then removed by evaporation under reduced pressure and the residue was dissolved in 200 mL of methylene chloride. The solution obtained was extracted 2 times with 100 mL of 1N HCl and once with 100 mL of water, dried over MgSO$_4$, filtered, and concentrated by evaporation under reduced pressure to obtain a white solid. This solid was stirred with 200 mL of hexane and filtered to give 1.62 g (52 percent yield) of the title compound as a white solid melting at 126°–129° C. (d).

What is claimed is:

1. A process for the preparation of an N-(aryl)-1,2,4-triazolopyrimidine-2-sulfonamide of the formula (V):

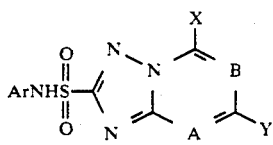

wherein
one of A or B is N and the other is C-Z,
X represents H, R, OR, SR or $CF_3$,
Y represents H, R, OR, F, Cl, Br or $CF_3$,
Z represents H, R, OR, F, Cl, Br, $CF_3$ or phenyl,
R represents a lower alkyl group optionally substituted with one or more halogen or with a lower alkoxy group, and
Ar is a substituted phenyl group of the formula:

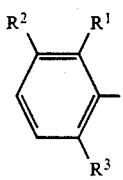

in which
$R^1$ represents H, F, Cl, Br, R, OR, SR or $CO_2R$,
$R^2$ represents H, R or OR,
$R^3$ represents H, F, Cl, Br, $CF_3$, $CO_2R$ or $NO_2$, and
R is as previously defined,
or Ar is a substituted pyrazole group (PRZ) of the formula:

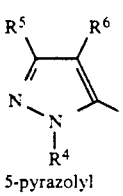

5-pyrazolyl

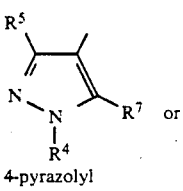

4-pyrazolyl or

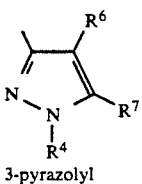

3-pyrazolyl in which
$R^4$ represents R, phenyl or pyridinyl,
$R^5$ represents H, $NO_2$ or $CF_3$,
$R^6$ represents H, F, Cl, Br, I or $CO_2R$,
$R^7$ represents H or R, and
R is as previously defined, consisting of contacting a substituted 1,2,4-triazolopyrimidine-2-sulfonyl halide of the formula

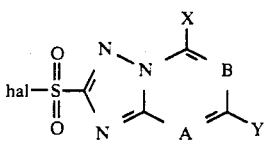

wherein
A, B, X, Y, Z and R are as previously defined, with an aryl amine of the formula $ArNH_2$ wherein
Ar is as previously defined,
in an inert aprotic organic solvent in the presence of a pyridine base and of a catalytic amount of dimethyl sulfoxide (DMSO).

2. The process of claim 1 in which A is C-Z and B is N.

3. The process of claim 1 in which A is N and B is C-Z.

4. The process of claim 1 in which X represents H, $CH_3$, $CH_2CH_3$, $OCH_3$ or $OCH_2CH_3$; Y represents H, $CH_3$, $CH_2CH_3$, $OCH_3$, $OCH_2CH_3$, F or Cl; and Z represents H, $CH_3$, $CH_2CH_3$, $OCH_3$, $OCH_2CH_3$, F, Cl or Br.

5. The process of claim 1 in which Ar is a substituted phenyl group of the formula:

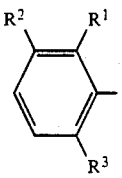

in which
$R^1$ represents F, Cl or $CH_3$,
$R^2$ represents H or $CH_3$, and
$R^3$ represents F, Cl $CF_3$, $CO_2CH_3$ or $NO_2$.

6. The process of claim 1 in which Ar is a substituted pyrazole group (PRZ) of the formula:

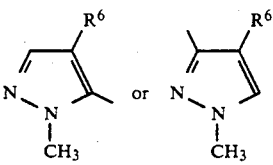

5-pyrazolyl    3-pyrazolyl in which
$R^6$ represents H, F, Cl, Br or I.

7. The process of claim 1 in which the substituted 1,2,4-triazolopyrimidine-2-sulfonyl halide is the sulfonyl chloride.

8. The process of claim 2 in which X is $OCH_3$.

9. The process of claim 3 in which Z is H.

* * * * *